US012259353B2

(12) United States Patent
Bedau

(10) Patent No.: US 12,259,353 B2
(45) Date of Patent: Mar. 25, 2025

(54) AMPLIFIERS FOR BIOLOGICAL SENSING APPLICATIONS

(71) Applicant: Western Digital Technologies, Inc., San Jose, CA (US)

(72) Inventor: Daniel Bedau, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 409 days.

(21) Appl. No.: 17/659,688

(22) Filed: Apr. 19, 2022

(65) Prior Publication Data

US 2023/0333049 A1 Oct. 19, 2023

(51) Int. Cl.
*G01N 27/414* (2006.01)
*G01N 33/487* (2006.01)

(52) U.S. Cl.
CPC ..... *G01N 27/4145* (2013.01); *G01N 27/4146* (2013.01); *G01N 33/48721* (2013.01)

(58) Field of Classification Search
CPC .......... G01N 27/4145; G01N 27/4146; G01N 33/48721
See application file for complete search history.

(56) References Cited

U.S. PATENT DOCUMENTS

| | | |
|---|---|---|
| 7,075,161 B2 | 7/2006 | Barth |
| 8,860,438 B2 | 10/2014 | Zhang |
| 9,217,727 B2 | 12/2015 | Rosenstein et al. |
| 9,650,670 B2 | 5/2017 | Kim et al. |
| 9,869,702 B2 | 1/2018 | Kuramochi |
| 9,914,966 B1* | 3/2018 | Dimitrov ............. C12Q 1/6874 |
| 11,009,498 B2 | 5/2021 | Alden et al. |
| 11,181,504 B2 | 11/2021 | Washizu |

(Continued)

FOREIGN PATENT DOCUMENTS

| | | |
|---|---|---|
| CN | 111090002 A | 5/2020 |
| CN | 107533045 B | 10/2020 |

(Continued)

OTHER PUBLICATIONS

A. Balan et al., "Improving Signal-to-Noise Performance for DNA Translocation in Solid-State Nanopores at MHz Bandwidths," Nano Lett. 2014, 14, 12, 7215-20, Nov. 21, 2014.

(Continued)

*Primary Examiner* — Fernando L Toledo
*Assistant Examiner* — Marshall Mu-Nuo Hatfield
(74) *Attorney, Agent, or Firm* — Jacobsen IP Law; Krista S. Jacobsen

(57) ABSTRACT

Disclosed herein are devices, systems, and methods can improve the signal-to-noise ratio of measurements made in biological applications. In some embodiments, an amplifier circuit that comprises a three-terminal device is situated in a configuration (e.g., a common-base or similar configuration) that allows the circuit to detect current through a nanopore while providing feedback to the sense electrode to reduce parasitic capacitance between the sense electrode and the counter electrode. The amplifier circuit may include, for example, a bi-polar junction transistor (BJT), a diamond transistor, a CMOS transistor, an operational transconductance amplifier, a voltage-controlled current source, a transconductor, a macro transistor, and/or a second-generation current conveyor (CCII+).

36 Claims, 9 Drawing Sheets

(56) References Cited

U.S. PATENT DOCUMENTS

| | | | |
|---|---|---|---|
| 2008/0248561 A1 | | 10/2008 | Golovchenko et al. |
| 2013/0341192 A1 | | 12/2013 | Dunbar et al. |
| 2015/0129936 A1* | | 5/2015 | Huang ............... G01N 27/4145 |
| | | | 257/253 |
| 2018/0074039 A1* | | 3/2018 | Soper ................ B01L 3/502761 |
| 2018/0275088 A1* | | 9/2018 | Huff .................... B01L 3/50273 |
| 2020/0292594 A1 | | 9/2020 | Hsu et al. |
| 2021/0172929 A1* | | 6/2021 | Alexander ........... C12Q 1/6874 |
| 2021/0300750 A1 | | 9/2021 | Waterman |
| 2021/0331168 A1* | | 10/2021 | Ma .................... B01L 3/502707 |

FOREIGN PATENT DOCUMENTS

| | | | | |
|---|---|---|---|---|
| CN | 112924745 A | | 6/2021 | |
| EP | 2734839 A1 | | 5/2014 | |
| EP | 2815425 A4 | | 10/2015 | |
| EP | 2815425 A4 | | 10/2015 | |
| KR | 20200144711 A | * | 12/2020 | .............. B01J 19/08 |
| WO | 2014066909 A1 | | 5/2014 | |
| WO | 2014066909 A1 | | 5/2014 | |

OTHER PUBLICATIONS

B. Goldstein, D. Kim, M. Magoch, Y. Astier and E. Culurciello, "CMOS low current measurement system for nanopore sensing applications," 2011 IEEE Biomedical Circuits and Systems Conference (BioCAS), 2011, pp. 265-268, doi: 10.1109/BioCAS.2011.6107778.

Beamish, E., Kwok, H., Tabard-Cossa, V., Godin, M. "Fine-tuning the Size and Minimizing the Noise of Solid-state Nanopores." J. Vis. Exp. (80), e51081, doi: 10.3791/51081 (2013).

C. Hoyle and A. Peyton, "Bootstrapping techniques to improve the bandwidth of transimpedance amplifiers," IEE Colloquium on Analog Signal Processing (Ref. No. 1998/472), 1998, pp. 7/1-7/6, doi: 10.1049/ic: 19980849.

Camilla L.C. Ip et al., "MinION Analysis and Reference Consortium: Phase 1 data release and analysis," F1000Research 2015, 4:1075 Last updated: May 23, 2017.

Ciccarella, P., Carminati, M., Ferrari, G., Fraccari, R.L., & Bahrami, A. "Integrated low-noise current amplifier for glass-based nanopore sensing." 2014 10th Conference on Ph.D. Research in Microelectronics and Electronics (PRIME), 1-4 (2014).

A. Balan et al., "Improving Signal-to-Noise Performance for DNA Translocation in Solid-State Nanopores at MHZ Bandwidths," Nano Lett. 2014, 14, 12, 7215-20, Nov. 21, 2014.

B. Goldstein, D. Kim, M. Magoch, Y. Astier and E. Culurciello, "CMOS low current measurement system for nanopore sensing applications," 2011 IEEE Biomedical Circuits and Systems Conference (BioCAS), 2011, pp. 265-268, doi: 10.1109/BioCAS.2011.6107778.

B. Luan, "Slowing and controlling the translocation of DNA in a solid-state nanopore," Nov. 2011, Nanoscale 4(4): 1068-77, DOI:10.1039/c1nr11201e.

Beamish, E., Kwok, H., Tabard-Cossa, V., Godin, M. "Fine-tuning the Size and Minimizing the Noise of Solid-state Nanopores." J. Vis. Exp. (80), e51081, doi: 10.3791/51081 (2013).

C. Hoyle and A. Peyton, "Bootstrapping techniques to improve the bandwidth of transimpedance amplifiers," IEE Colloquium on Analog Signal Processing, 1998, pp. 7/1-7/6, doi: 10.1049/ic: 19980849.

Camilla L.C. Ip et al., "MinION Analysis and Reference Consortium: Phase 1 data release and analysis," 1000Research 2015, 4:1075 Last updated: May 23, 2017.

Ciccarella, P., Carminati, M., Ferrari, G., Fraccari, R.L., & Bahrami, A. "Integrated low-noise current amplifier for glass- based nanopore sensing." 2014 10th Conference on Ph.D. Research in Microelectronics and Electronics (PRIME), 1-4 (2014).

D. V. Barkovaa et al., "Channel and Motor Proteins for Translocation of Nucleic Acids in Nanopore Sequencing," ISSN 0027-1314, Moscow University Chemistry Bulletin, 2020, vol. 75, No. 3, pp. 149-161.

Electrical Engineering Stack Exchange, Is the OPA860 a diamond transistor?, Mar. 2017.

J. Rosenstein, V. Ray, M. Drndic and K. L. Shepard, "Solid-state nanopores integrated with low-noise preamplifiers for high-bandwidth DNA analysis," 2011 IEEE/NIH Life Science Systems and Applications Workshop (LiSSA), 2011, pp. 59-62, doi: 10.1109/LISSA.2011.5754155.

L. Liu et al., "DNA-Based Nanopore Sensing," Sep. 27, 2016, https://doi.org/10.1002/anie.201604405.

P. Horowitz and W. Hill, "The Art of Electronics, 3rd Edition," Cambridge University Press, 2015.

Patrick S Spinney et al., "Fabrication and characterization of a solid-state nanopore with self-aligned carbon nanoelectrodes for molecular detection," Nanotechnology, vol. 23, No. 13, 2012.

Rosenstein, J., Wanunu, M., Merchant, C. et al. "Integrated nanopore sensing platform with sub-microsecond temporal resolution." Nat Methods 9, 487-492 (2012). https://doi.org/10.1038/nmeth.1932.

S. Magierowski et al., "Nanopore-CMOS Interfaces for DNA Sequencing," Biosensors (Basel), Aug. 6, 2016;6(3):42. doi: 10.3390/bios6030042.

S. Shekar et al., "Measurement of DNA Translocation Dynamics in a Solid-State Nanopore at 100 ns Temporal Resolution," Nano Lett. 2016, 16, 7, 4483-89, Jun. 22, 2016.

Shengfa Liang et al., "Noise in nanopore sensors: Sources, models, reduction, and benchmarking," Nanotechnology and Precision Engineering 3 (2020) 9-17.

Stephen Jordan Fleming, "Probing nanopore—DNA interactions with MspA," Nov. 2017.

* cited by examiner

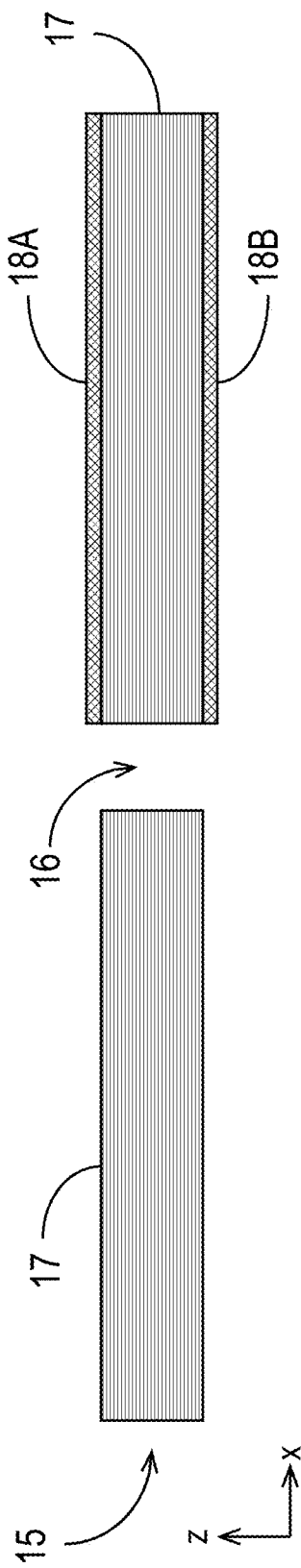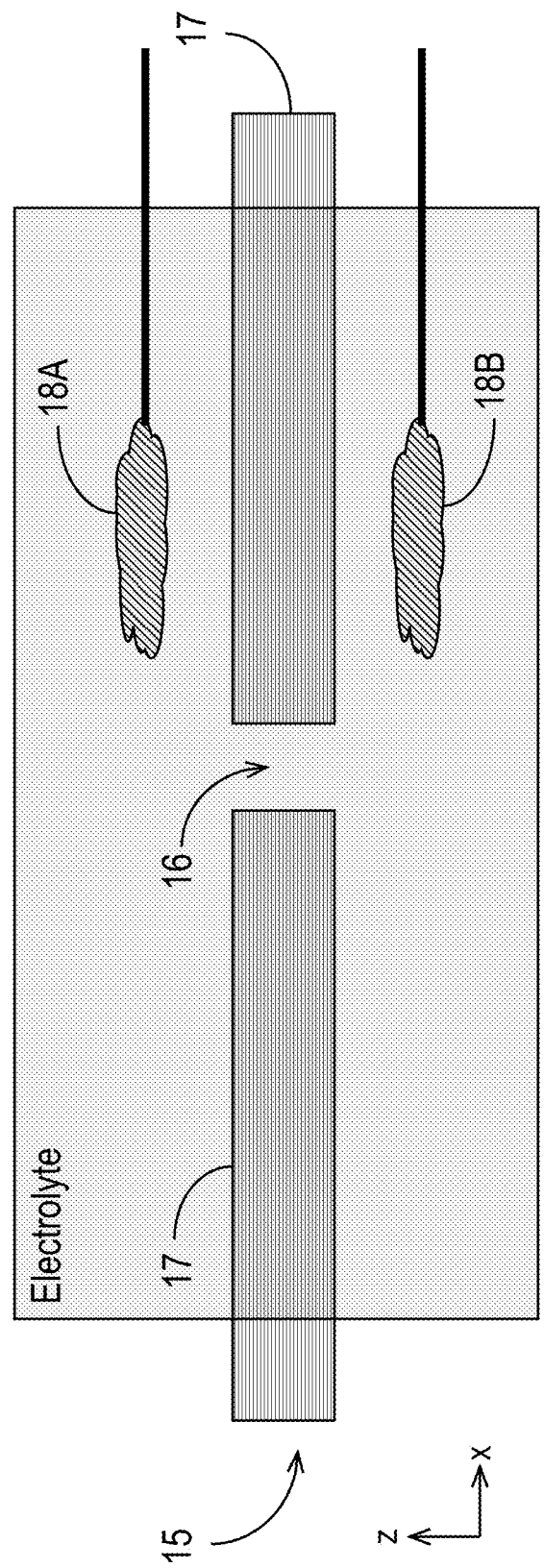
FIG. 3A
FIG. 3B

AMPLIFIERS FOR BIOLOGICAL SENSING APPLICATIONS

BACKGROUND

Nanopores are small holes, typically 1-2 nanometers (nm) in diameter and a couple of nanometers thick, that can be used to observe single molecules at high throughput and with relatively fine temporal resolution. Nanopores can be used to read molecules (e.g., biomolecules) for applications such as DNA sequencing, DNA/RNA storage applications, and bioanalytical sensing.

There are two types of nanopore: biological nanopores (also referred to as protein nanopores) and solid-state nanopores. A biological nanopore is made from a pore material embedded in a lipid membrane. A solid-state nanopore is a nanoscale (e.g., nanometer-sized) opening in a synthetic membrane (e.g., SiNx, $SiO_2$, etc.).

A target molecule in an electrolyte solution can be driven through a nanopore (either biological or solid-state) by electrophoresis. A highly-focused external electric field applied transverse to and in the vicinity of the nanopore (e.g., by electrodes used to read or detect the molecule) acts on a relatively short segment of the negatively charged molecule and directs it through the hole in the nanopore.

An ionic (or tunnel) current can be generated across the nanopore by applying a bias voltage. As a molecule passes through a nanopore, the ions occupying the pore are displaced, which causes changes in the current measured across the nanopore. These changes in the current can be observed and used to detect constituent parts of the molecule (e.g., nucleotides of a DNA strand). For example, by analyzing the amplitudes, durations, frequencies, and/or shapes of the blockade events, various properties of the target molecule can be deduced.

As a specific example, as nucleic acid moves, or translocates, through a nanopore, different nucleotides cause different current patterns. Specifically, the nucleotides cause distinct, measurable current blockades, or current drops, as they pass through the nanopore. The current blockades can be recorded (e.g., using a current amplifier) and converted into digital signals (e.g., using an analog-to-digital converter). These current blockades, or patterns of them, can be used to distinguish between different nucleotides.

One challenge with using nanopores is that detection relies on the ability to detect small differences in the current (e.g., on the order of picoamperes) as a molecule translocates through the nanopore. Noise in the current measurement limits the signal-to-noise ratio (SNR) and the effective time resolution of the detection. The noise is dependent on any capacitance present at the input to the amplifier that senses and amplifies the current signal. For solid-state nanopores, the total capacitance includes the capacitance of the thin membrane in which the nanopore is fabricated, the capacitance of the wiring between the electrodes and the amplifier, and the characteristic capacitance of the amplifier at its input. The capacitance at the input to the amplifier forms a pole with the output impedance of the amplifier. High capacitance at the input to the amplifier can cause noise peaking and SNR degradations.

Thus, there is a need to reduce noise in the detected current.

SUMMARY

This summary represents non-limiting embodiments of the disclosure.

In some aspects, the techniques described herein relate to a system for detecting molecules, the system including: a nanopore unit including a nanopore, a sense electrode, and a counter electrode; and an amplifier circuit coupled to the nanopore unit, the amplifier circuit including a three-terminal device, wherein a first terminal of the three-terminal device is low impedance and coupled to the sense electrode, a second terminal of the three-terminal device is high impedance and coupled to a bias voltage source, and a third terminal of the three-terminal device is a high-impedance output of the amplifier circuit, wherein: an impedance of the first terminal is less than an impedance of the second terminal; the impedance of the first terminal is less than an impedance of the third terminal; the sense electrode is configured to, in cooperation with the counter electrode, detect a current associated with the nanopore, and provide the detected current to the first terminal of the three-terminal device; and the third terminal of the three-terminal device is configured to provide a signal representing the detected current to a downstream component.

In some aspects, the techniques described herein relate to a system, wherein the downstream component is a digitizer, and wherein the digitizer coupled is coupled to the third terminal of the three-terminal device and is configured to generate a digitized signal from the signal representing the detected current.

In some aspects, the techniques described herein relate to a system, further including a processor coupled to an output of the digitizer.

In some aspects, the techniques described herein relate to a system, wherein three-terminal device includes a bi-polar junction transistor (BJT), and wherein the first terminal is an emitter of the BJT, the second terminal is a base of the BJT, and the third terminal is a collector of the BJT.

In some aspects, the techniques described herein relate to a system, wherein the BJT is integrated onto a substrate of the nanopore.

In some aspects, the techniques described herein relate to a system, wherein three-terminal device includes a diamond transistor, and wherein the first terminal is an E terminal of the diamond transistor, the second terminal is a B terminal of the diamond transistor, and the third terminal is a C terminal of the diamond transistor.

In some aspects, the techniques described herein relate to a system, wherein the diamond transistor is integrated onto a substrate of the nanopore.

In some aspects, the techniques described herein relate to a system, wherein the three-terminal device includes at least one of: a bi-polar junction transistor (BJT), a diamond transistor, a CMOS transistor, an operational transconductance amplifier, a voltage-controlled current source, a transconductor, a macro transistor, or a second-generation current conveyor (CCII+).

In some aspects, the techniques described herein relate to a system, wherein the nanopore unit is a first nanopore unit, the nanopore is a first nanopore, the sense electrode is a first sense electrode, and the counter electrode is a first counter electrode, and further including: a multiplexer situated between and coupled to the first nanopore unit and the first terminal of the three-terminal device; a second nanopore unit including a second nanopore, a second sense electrode, and a second counter electrode, wherein the second sense electrode is coupled to the multiplexer; and control logic coupled to the multiplexer and configured to select one of the first sense electrode or the second sense electrode.

In some aspects, the techniques described herein relate to a system, further including: drive circuitry coupled to the first nanopore unit and to the second nanopore unit and configured to create a first potential between the first sense electrode and the first counter electrode and/or create a second potential between the second sense electrode and the second counter electrode.

In some aspects, the techniques described herein relate to a system, wherein the downstream component is a digitizer, and wherein the digitizer coupled is coupled to the third terminal of the three-terminal device and is configured to generate a digitized signal from the signal representing the detected current.

In some aspects, the techniques described herein relate to a system, further including a processor coupled to an output of the digitizer.

In some aspects, the techniques described herein relate to a system, wherein the first counter electrode and the second counter electrode are coupled to a common bias voltage source.

In some aspects, the techniques described herein relate to a system, wherein the first counter electrode and the second counter electrode are a same electrode.

In some aspects, the techniques described herein relate to a system for detecting molecules, the system including: a nanopore array including a plurality of nanopore units, each of the plurality of nanopore units including a respective nanopore, a respective sense electrode, and a respective counter electrode, each respective sense electrode for detecting a current associated with the respective nanopore; a multiplexer coupled to the nanopore array; an amplifier circuit coupled to an output of the multiplexer, the amplifier circuit including a three-terminal device, wherein a first terminal of the three-terminal device is coupled to the output of the multiplexer, a second terminal of the three-terminal device is coupled to a bias voltage source, and a third terminal of the three-terminal device is an output of the amplifier circuit; and control logic coupled to the multiplexer and configured to control the multiplexer to select a particular nanopore unit of the plurality of nanopore units and to couple the respective sense electrode of the particular nanopore unit to the amplifier circuit, wherein the particular nanopore unit is any one of the plurality of nanopore units.

In some aspects, the techniques described herein relate to a system, further including drive circuitry coupled to the nanopore array.

In some aspects, the techniques described herein relate to a system, wherein the three-terminal device includes a bi-polar junction transistor (BJT), and wherein the first terminal is an emitter of the BJT, the second terminal is a base of the BJT, and the third terminal is a collector of the BJT.

In some aspects, the techniques described herein relate to a system, wherein the three-terminal device includes a diamond transistor, and wherein the first terminal is an E terminal of the diamond transistor, the second terminal is a B terminal of the diamond transistor, and the third terminal is a C terminal of the diamond transistor.

In some aspects, the techniques described herein relate to a system, wherein the three-terminal device includes at least one of: a bi-polar junction transistor (BJT), a diamond transistor, a CMOS transistor, an operational transconductance amplifier, a voltage-controlled current source, a transconductor, a macro transistor, or a second-generation current conveyor (CCII+).

In some aspects, the techniques described herein relate to a system, wherein the first terminal is a low-impedance terminal, the second terminal is a high-impedance terminal, and the third terminal is a current source terminal.

In some aspects, the techniques described herein relate to a system, wherein the control logic is further configured to: control the multiplexer to select a second nanopore unit of the plurality of nanopore units for reading.

In some aspects, the techniques described herein relate to a system, wherein each respective counter electrode is coupled to a common voltage source.

In some aspects, the techniques described herein relate to a system, wherein each respective counter electrode is a same counter electrode.

In some aspects, the techniques described herein relate to a system, further including: a digitizer coupled to the output of the amplifier circuit, wherein the digitizer is configured to generate a digitized signal from the current associated with the respective nanopore.

In some aspects, the techniques described herein relate to a system, further including a processor coupled to an output of the digitizer.

In some aspects, the techniques described herein relate to a system, wherein the nanopore array is a first nanopore array, the plurality of nanopore units is a first plurality of nanopore units, the multiplexer is a first multiplexer, the amplifier circuit is a first amplifier circuit, and the three-terminal device is a first three-terminal device, and further including: a second nanopore array including a second plurality of nanopore units, each of the second plurality of nanopore units including a respective nanopore, a respective sense electrode, and a respective counter electrode, each respective sense electrode for detecting a current associated with the respective nanopore; a second multiplexer coupled to the second nanopore array; and a second amplifier circuit coupled to an output of the second multiplexer, the second amplifier circuit including a second three-terminal device, wherein a first terminal of the second three-terminal device is coupled to the output of the second multiplexer, a second terminal of the second three-terminal device is coupled to the bias voltage source, and a third terminal of the second three-terminal device is an output of the second amplifier circuit, and wherein the control logic is further coupled to the second multiplexer and is configured to control the second multiplexer to select a particular nanopore unit of the second plurality of nanopore units and to couple the respective sense electrode of the particular nanopore unit of the second plurality of nanopore units to the second amplifier circuit, wherein the particular nanopore unit of the second plurality of nanopore units is any one of the second plurality of nanopore units.

In some aspects, the techniques described herein relate to a system, wherein: the first three-terminal device includes a first bi-polar junction transistor (BJT), wherein the first terminal of the first three-terminal device is an emitter of the first BJT, the second terminal of the first three-terminal device is a base of the first BJT, and the third terminal of the first three-terminal device is a collector of the first BJT, and the second three-terminal device includes a second BJT, wherein the first terminal of the second three-terminal device is an emitter of the second BJT, the second terminal of the second three-terminal device is a base of the second BJT, and the third terminal of the second three-terminal device is a collector of the second BJT.

In some aspects, the techniques described herein relate to a system, wherein: the first three-terminal device includes a first diamond transistor, wherein the first terminal of the first three-terminal device is an E terminal of the first diamond transistor, the second terminal of the first three-terminal device is a B terminal of the first diamond transistor, and the third terminal of the first three-terminal device is a C terminal of the first diamond transistor, and the second three-terminal device includes a second diamond transistor, wherein the first terminal of the second three-terminal device is an E terminal of the second diamond transistor, the second terminal of the second three-terminal device is a B terminal of the second diamond transistor, and the third terminal of the second three-terminal device is a C terminal of the first diamond transistor.

In some aspects, the techniques described herein relate to a system, wherein the first three-terminal device and/or the second three-terminal device includes at least one of: a bi-polar junction transistor (BJT), a diamond transistor, a CMOS transistor, an operational transconductance amplifier, a voltage-controlled current source, a transconductor, a macro transistor, or a second-generation current conveyor (CCII+).

In some aspects, the techniques described herein relate to a system, wherein: each respective counter electrode of the first nanopore array is coupled to a first common voltage source, and each respective counter electrode of the second nanopore array is coupled to a second common voltage source.

In some aspects, the techniques described herein relate to a system, wherein the first common voltage source and the second common voltage source are a same voltage source.

In some aspects, the techniques described herein relate to a system, wherein: each respective counter electrode of the first nanopore array is a first common counter electrode; and each respective counter electrode of the second nanopore array is a second common counter electrode.

In some aspects, the techniques described herein relate to a system, wherein each respective counter electrode of the first nanopore array and each respective counter electrode of the second nanopore array is a common counter electrode.

In some aspects, the techniques described herein relate to a system, further including: a first digitizer coupled to the output of the first amplifier circuit; a second digitizer coupled to the output of the second amplifier circuit; and a processor coupled to a first output of the first digitizer and to a second output of the second digitizer.

BRIEF DESCRIPTION OF THE DRAWINGS

Objects, features, and advantages of the disclosure will be readily apparent from the following description of certain embodiments taken in conjunction with the accompanying drawings in which:

FIG. 3A illustrates a cross-section of an example configuration of a nanopore and the sense electrode and counter electrode in accordance with some embodiments.

FIG. 3B illustrates a cross-section of an alternative example configuration of a nanopore and the sense electrode and counter electrode in accordance with some embodiments.

Figure 1:
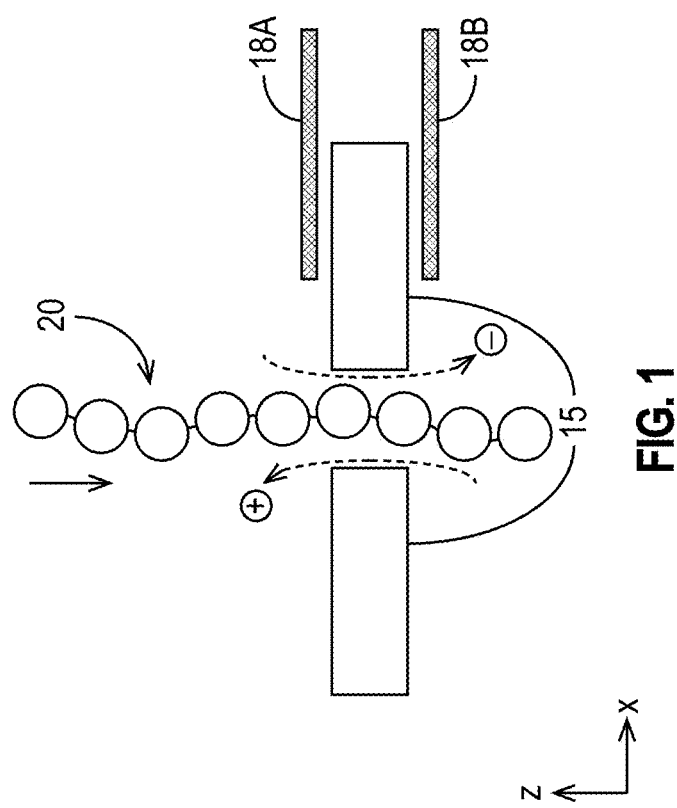
FIG. 1 illustrates a nanopore with a molecule passing through it in accordance with some embodiments.

To facilitate understanding, identical reference numerals have been used, where possible, to designate identical elements that are common to the figures. It is contemplated that elements disclosed in one embodiment may be beneficially utilized in other embodiments without specific recitation. Moreover, the description of an element in the context of one drawing is applicable to other drawings illustrating that element.

DETAILED DESCRIPTION

Disclosed herein are amplifiers suitable for biological sensing applications, such as those using nanopores. The disclosed amplifier circuits can substantially reduce amplifier input current noise. Also disclosed herein are devices, and systems, and methods of using the amplifier circuits, e.g., in biological sensing applications.

FIG. 1 illustrates a nanopore 15 with a molecule 20 (e.g., a single-stranded DNA (ssDNA) molecule), passing through it. Two electrodes, which are referred to herein as the sense electrode 18A and the counter electrode 18B, are situated near the nanopore 15 to, in cooperation, sense the ionic or tunnel current through (or associated with) the nanopore 15. The sense electrode 18A and/or counter electrode 18B are typically connected to a voltage source (not illustrated), which creates a potential between the sense electrode 18A and counter electrode 18B.

Figure 2:
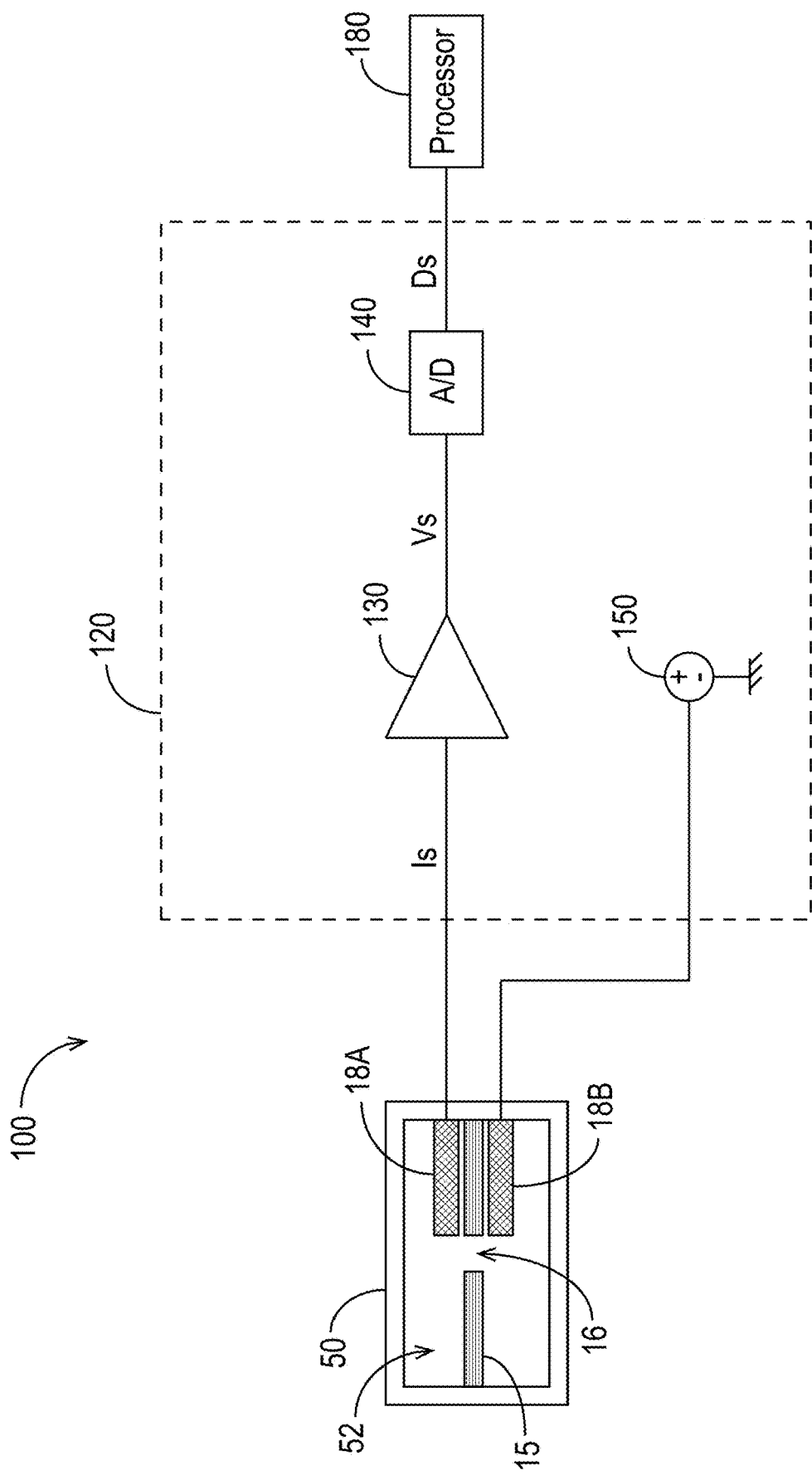
FIG. 2 is a diagram of a system for detecting molecules in accordance with some embodiments.

FIG. 2 is a diagram of a system 100 for detecting molecules in accordance with some embodiments. The system 100 includes a nanopore unit 50, a detection device 120, and a processing device 180. The illustrated nanopore unit 50 has a fluid chamber 52 that can be filled with an electrolyte solution containing molecules to be detected (e.g., molecule 20 from FIG. 1). The nanopore unit 50 includes a nanopore 15 with a hole 16. The sense electrode 18A and counter electrode 18B are situated on either side of the nanopore 15, as illustrated. As explained further below, the sense electrode 18A and/or counter electrode 18B may be in contact with the nanopore 15 or they may be separated from it.

In the diagram of FIG. 2, the detection device 120 comprises an amplifier 130, an analog-to-digital converter 140 (or, more generally, a digitizer), and a voltage source 150. The amplifier 130 may be, for example, a transimpedance amplifier that is configured to convert the detected current, Is, to a voltage, Vs. The analog-to-digital converter 140 is configured to digitize the output voltage, Vs, of the amplifier 130 and provide it to the processing device 180 (e.g., via an interface). The voltage source 150 is configured to generate a voltage of sufficient magnitude across the sense electrode 18A and counter electrode 18B to drive molecules within the fluid chamber 52 into the hole 16 and to allow the effect of the molecules on the current to be detected by the amplifier 130. The voltage source 150 may be capable of providing a variable voltage level Vb across the sense electrode 18A and counter electrode 18B. The amplifier 130 may operate by, for example, detecting the resistance between the sense electrode 18A and the counter electrode 18B when the voltage is applied by the voltage source 150.

In operation, the voltage source 150 generates a voltage across the sense electrode 18A and counter electrode 18B, which causes an ionic or tunnel current, Is, to flow between the sense electrode 18A and counter electrode 18B and also causes molecules in the fluid chamber 52 to be drawn into the hole 16 of the nanopore 15. If the voltage across the sense electrode 18A and counter electrode 18B is Vb, the current Is is given by Ohm's law: Is=Vb/Rp, where Rp is the resistance through the nanopore 15 encountered by a molecule 20 as it passes through the hole 16. The amplifier 130 converts the current Is to a voltage, Vs, which it passes to the analog-to-digital converter 140. The voltage Vs is dependent on the gain of the amplifier 130. The analog-to-digital converter 140 converts the voltage signal Vs into digital data Ds, which it passes to the processing device 180, which may be situated in a different (external) physical device than the nanopore unit 50 and/or detection device 120 (e.g., the nanopore unit 50 and/or detection device 120 may be situated on/in a single integrated circuit device, and the processing device 180 may be in a computer or other device external to the integrated circuit device). The analog-to-digital converter 140 may provide the sampled signal Ds to the processing device 180 using any available communication path (e.g., wired or wireless) and in accordance with any suitable protocol (e.g., IEEE 802.11, Ethernet, USB, etc.).

As described further below, multiple instantiations of the nanopore unit 50, the detection device 120, and/or the processing device 180 may be included in a single physical device, or they may be separate. For example, the nanopore unit 50 and the detection device 120 may be included in a single device that is connected to the processing device 180 (e.g., a computer or other processor). In addition, a system may include multiple nanopores 15 connected to sense electrodes 18A and counter electrodes 18B (which may be dedicated or shared), in turn coupled to detection devices 120 (which may be dedicated or shared) that measure the respective currents (Is).

FIG. 3A illustrates a cross-section of an example configuration of a nanopore 15 and the sense electrode 18A and counter electrode 18B in accordance with some embodiments. The cross-section is in the x-z plane, as indicated by the axes. As illustrated in the example of FIG. 3A, the nanopore 15 can comprise a thin dielectric layer 17 with a hole 16 and two electrodes, namely, the sense electrode 18A and counter electrode 18B, attached to the sides of the nanopore 15. The sense electrode 18A and counter electrode 18B may have thicknesses in the z-direction of, for example, around 10 nm.

FIG. 3B illustrates a cross-section of an alternative example configuration of a nanopore 15 and the sense electrode 18A and counter electrode 18B in accordance with some embodiments. As illustrated in FIG. 3B, the sense electrode 18A and counter electrode 18B can be electrochemical electrodes, e.g. silver/silver-chloride pairs.

With either of the sense electrode 18A and counter electrode 18B embodiments illustrated in FIGS. 3A and 3B, the thin dielectric layer 17 of the nanopore 15 is very thin (e.g., in the nm range) to create a nanopore 15 with a suitable aspect ratio so that molecules passing through the hole 16 will cause measurable disturbances in the current. As a result, the capacitance between the sense electrode 18A and counter electrode 18B, which is inversely proportional to the thickness of the thin dielectric layer 17, is naturally very large. This capacitance can amplify the noise of the applied voltage Vb by forming a pole with the output impedance of the amplifier 130. It can also cause the detection device 120 to have an unstable dynamic response at higher frequencies. This instability can reduce the usefulness of the system 100 by preventing it from being able to detect rapid changes in the current as molecules pass through the nanopore 15 at the applied voltage Vb. Specifically, the capacitance amplifies the noise voltage, particularly at higher frequencies. The amplified noise limits the frequency at which the nanopore 15 can read or detect molecules passing through its hole 16.

Figure 4:
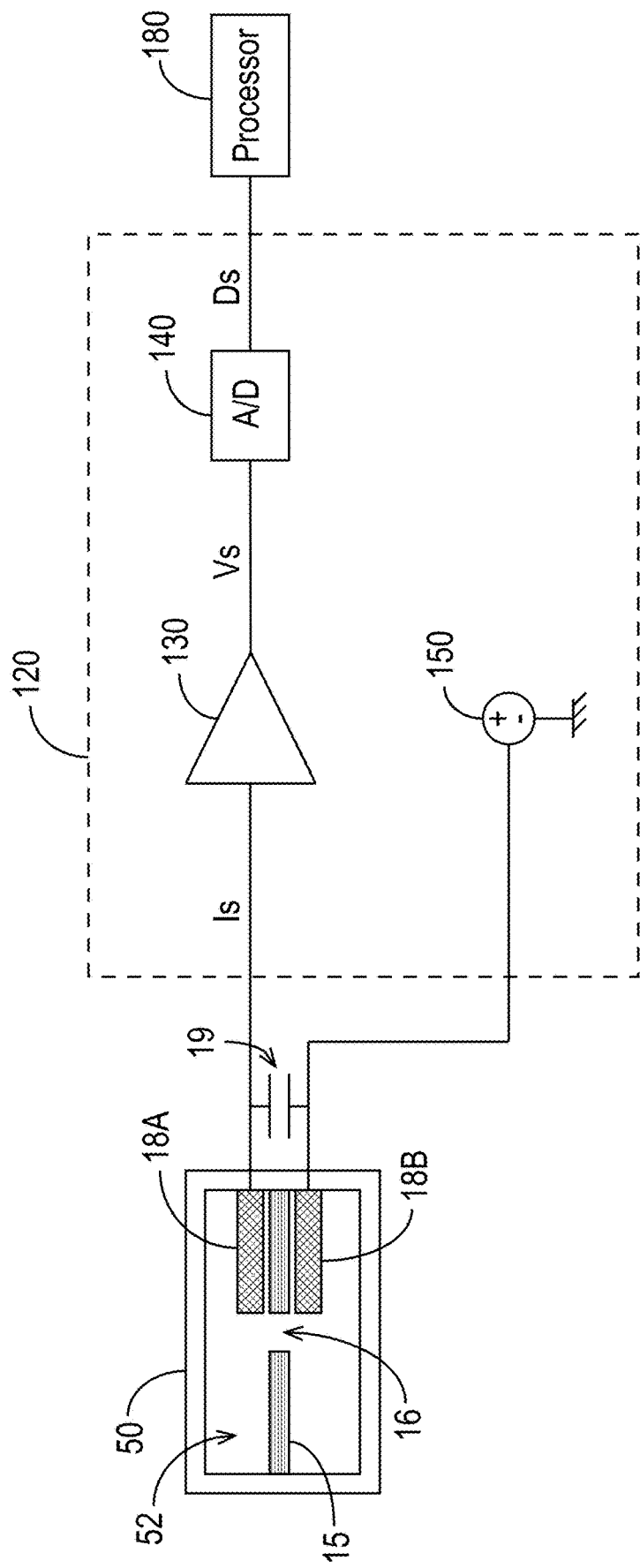
FIG. 4 is a conceptual illustration of the system of FIG. 2 representing the capacitance between the sense electrode and the counter electrode as a capacitor.

The capacitance of the nanopore 15 can be modeled as the parallel-plate capacitance of the constituent elements of the nanopore unit 50. FIG. 4 is a conceptual illustration of the system 100 of FIG. 2 representing the capacitance between the sense electrode 18A and the counter electrode 18B as a capacitor. As illustrated in FIG. 4, the capacitance can be considered as a parasitic capacitance 19 between the sense electrode 18A and counter electrode 18B. The parasitic capacitance 19 acts as a charge sink for the sense electrode 18A and can create a peak in the noise spectrum. For example, if a potential difference $\Delta U$ is created between the sense electrode 18A and counter electrode 18B, a charge $Q=\Delta U*C$ flows into the parasitic capacitance 19, which reduces the signal (e.g., the current Is) that is sensed by the amplifier 130 and, correspondingly, reduces the SNR of the measurement.

Prior approaches to improving the SNR have included reducing the capacitance of the nanopore 15 by modifying its physical layout, reducing the bandwidth of the amplifier 130, and reducing the translocation speed of the molecules passing through the nanopore 15. All of these approaches have drawbacks. For example, changes to the physical layout are limited by manufacturability, and reduced amplifier 130 bandwidth and/or translocation speed of molecules through the nanopore 15 reduces the rate at which molecules can be read. Therefore, there remains a need for additional solutions.

Disclosed herein are devices, systems, and methods that can improve the SNR of nanopore 15 measurements by mitigating the effect of the parasitic capacitance 19. In some embodiments, an amplifier circuit that comprises a three-terminal device (e.g., at least one transistor) is situated in a configuration that allows the circuit to read the nanopore 15 (e.g., detect the current Is) while providing feedback to the sense electrode 18A to reduce the parasitic capacitance 19 between the sense electrode 18A and the counter electrode 18B. The amplifier circuit may include, for example, a bi-polar junction transistor (BJT) situated in a common-base amplifier configuration. In some embodiments, the amplifier circuit includes a voltage-controlled current source or an integrated amplifier that uses the so-called "diamond" topology. The disclosed amplifier circuits both amplify the current from the sense electrode 18A and inject a charge into the sense electrode 18A to cancel at least part of the parasitic capacitance 19 to mitigate charge being diverted to the parasitic capacitance 19.

Referring again to FIG. 4, if the amplifier 130 is an inverting amplifier, the parasitic capacitance between the input and output of the amplifier 130 will appear to be multiplied by the gain of the amplifier. The additional amount of capacitance is known as Miller capacitance, and the apparent increase in input capacitance is known as the Miller effect. The Miller effect limits the bandwidth of the amplifier 130. Furthermore, the parasitic capacitance 19 between the sense electrode 18A and the counter electrode 18B will reduce the phase margin for stability of the detection device 120 and introduce noise gain at frequencies interfering with the response of the nanopore 15 to molecules. Both of these phenomena can limit the capabilities and/or effectiveness of the detection device 120.

The inventor of the techniques disclosed herein had the insight that the input noise effect can be avoided by an amplifier circuit that uses a three-terminal device, such as a BJT, a diamond transistor, or a similar device in a common-base configuration to provide wide bandwidth with reduced noise gain while reducing the parasitic capacitance 19 at the input. A common-base configuration is not subject to the Miller effect.

Figure 5A:
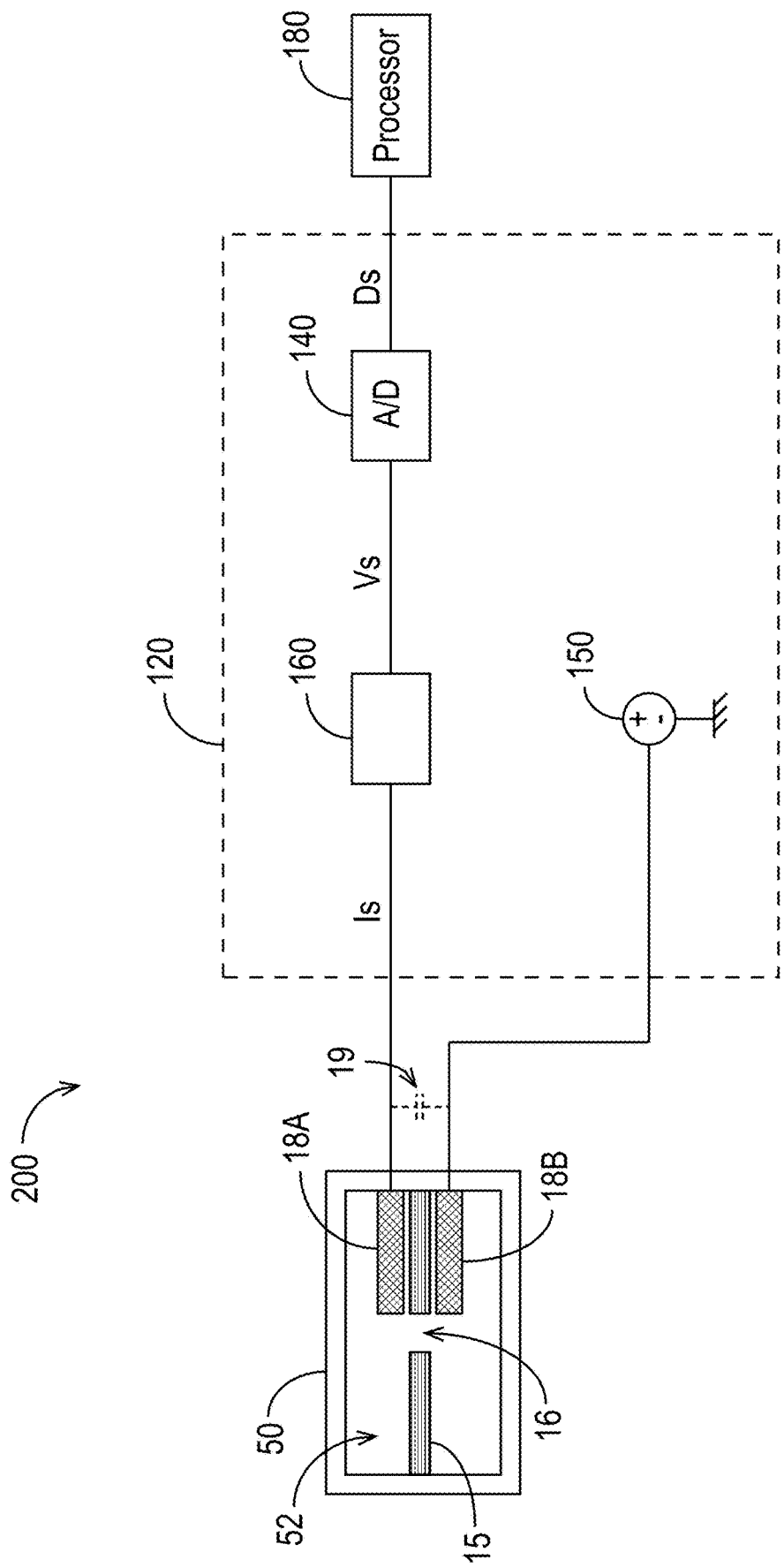
FIG. 5A is a diagram illustrating an example system in accordance with some embodiments.

FIG. 5A is a diagram illustrating an example system 200 in accordance with some embodiments. As shown in FIG. 5A, the current detected by the sense electrode 18A is measured by the amplifier circuit 160. The amplifier circuit 160 is coupled to and provides an output to the analog-to-digital converter 140. The analog-to-digital converter 140 is coupled to a processing device 180 and provides a digitized version of the read signal to the processing device 180.

One objective of the amplifier circuit 160 is to suppress the effects of the parasitic capacitance 19. Generally speaking, the amplifier circuit 160 includes a three-terminal device, examples of which are described further below in the context of FIGS. 5B, 5C, and 5D. A first terminal of the three-terminal device is a low-impedance terminal that is coupled to the sense electrode 18A, a second terminal of the three-terminal device is a high-impedance terminal that is coupled to a bias voltage source, and a third terminal of the three-terminal device is a high-impedance terminal that provides the output of the amplifier circuit 160. As used herein, the term "low-impedance" is used relative to and in contradistinction to the term "high-impedance." The impedance of a low-impedance terminal of a three-terminal device is lower than the impedance of a high-impedance terminal of a three-terminal device. Depending on the three-terminal device, the impedance of a low-impedance terminal may be, for example, on the order of a few Ohms to about 1 kΩ, and the impedance of a high-impedance terminal may be, for example, on the order of a few kΩ to GΩ. The sense electrode 18A detects a current of the nanopore 15 and provides it to the first terminal of the three-terminal device. The third terminal of the three-terminal device provides an amplified signal that represents the detected current to a downstream component (e.g., a digitizer (e.g., an analog-to-digital converter), a processor, etc.).

Figure 5C:
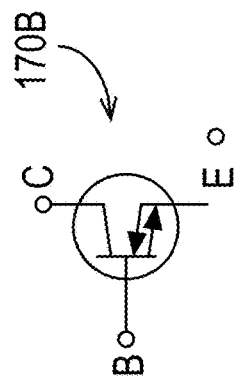
FIG. 5C illustrates an example of a diamond transistor that can be used in the amplifier circuit accordance with some embodiments.
Figure 5D:
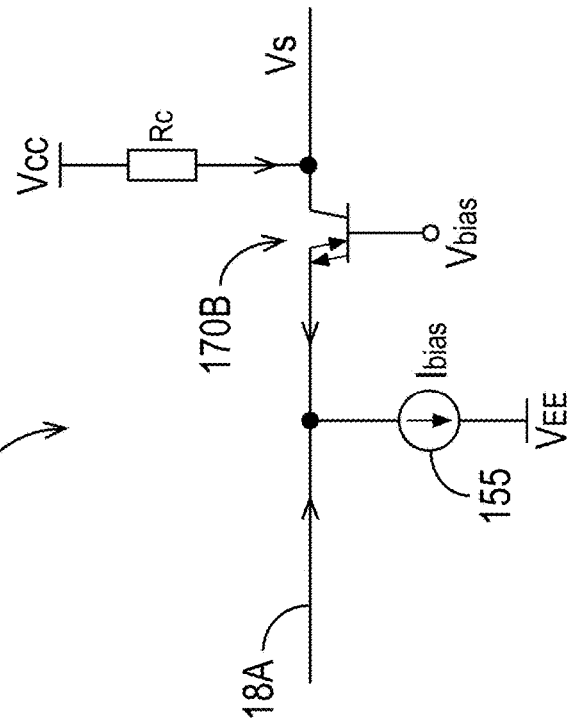
FIG. 5D illustrates an example of a circuit that includes a diamond transistor in accordance with some embodiments.
Figure 5B:
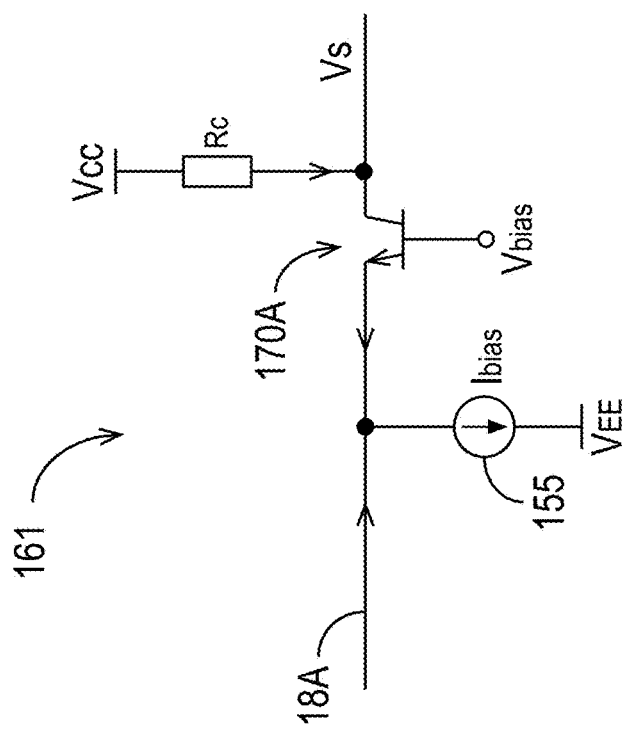
FIG. 5B is an example of a circuit that can be used as the amplifier circuit in FIG. 5A in accordance with some embodiments.

FIG. 5B is an example of a circuit 161 that can be used as the amplifier circuit 160 in FIG. 5A. The circuit 161 includes a BJT 170A with its emitter coupled to a current source 155 and the sense electrode 18A, its base coupled to a bias voltage, Vbias, and its collector coupled to Vcc through a resistor Rc and providing the output of the circuit 161. The circuit 161 is in a common-base (CB) amplifier configuration that provides a high-bandwidth current buffer with a low input impedance and a small feedback capacitance that does not suffer from the Miller effect.

A significant aspect of the circuit 161 is that the base is not grounded, but rather is connected to a bias voltage. With the circuit 161 as illustrated, the bias voltage biases the nanopore 15. Because the base of the BJT 170A is held at a constant bias voltage, Vbias, it shields the collector signal from being fed back to the emitter input. Thus, the circuit 161 provides a better high frequency response than other types of amplifier circuits that could be used in nanopore 15 applications.

In operation, whenever the current Is from the nanopore 15 is less than the current Ibias, the emitter current is positive, and the BJT 170A is in forward-active mode. As long as a sufficient bias voltage Vbias is applied (e.g., around 0.7 V for common types of BJTs), the voltage on the sense electrode 18A will be held close to 0 V as a result of the high forward transconductance of the BJT 170A. As a result, for both positive or negative voltages applied to the sense electrode 18A, the circuit 161 effectively presents a low impedance to ground as long as the sensed current Is is less than the bias current Ibias. The parasitic capacitance 19 is then divided by the transconductance of the circuit 161, thereby reducing the noise in reading the current Is from the nanopore 15.

In some embodiments, the bias voltage Vbias is selected so that the current Is is close to zero for an input voltage of close to zero. Using an approximate Ebers-Moll model of the BJT 170A, the bias voltage is $$-nV_T \log\left(\frac{I\text{bias}}{I{sat}} + 1\right),$$

where Isat is the saturation current of the base-emitter junction, $V_T$, which is approximately 26 mV, is the thermal voltage, and n is the diode ideality factor. The output of the circuit 161 then provides an amplified voltage signal Vs that is linearly related to the input current Is:

$$Is = I\text{bias} - \left(\frac{1+\beta}{\beta}\right)\left(\frac{Vcc - Vs}{R_C}\right)$$

where β is the forward common-emitter current gain of the BJT 170A.

As will be appreciated by those having ordinary skill in the art, packaged discrete BJTs for radio-frequency applications are available with very low parasitic capacitance, making them a good choice for the BJT 170A of the circuit 161.

In some embodiments, however, the BJT 170A is directly integrated onto the nanopore 15 substrate to mitigate the need for wiring and thereby reduce the input capacitance. As will be appreciated by those having ordinary skill in the art, BJTs are available in integrated processes, such as BiCMOS processes.

It is to be appreciated that the circuit 161 can alternatively be implemented using a common gate amplifier in pure CMOS. Such an implementation might have inferior input capacitance suppression, however, because a MOSFET generally has inferior transconductance.

In some embodiments, the amplifier circuit 160 uses a voltage-controlled current source or an integrated amplifier that uses a diamond topology. For example, the amplifier circuit 160 can include a diamond transistor, which may also be referred to as an operational transconductance amplifier, a voltage-controlled current source, a transconductor, a macro transistor, or a second-generation current conveyor (CCII+). The diamond transistor is a DC-coupled structure that acts as an ideal transistor and does not require biasing circuits or an external offset voltage compensation network. A diamond transistor, which provides high gain, can be used similarly to a CB amplifier.

FIG. 5C illustrates an example of a diamond transistor 170B that can be used in accordance with some embodiments. As shown in FIG. 5C, the diamond transistor 170B has three terminals, labeled as B, E, and C. The B terminal is a high-impedance terminal, the E terminal is a low-impedance terminal, and the C terminal is a high-impedance output current source terminal. One difference between the diamond transistor 170B and other transistors (e.g., the BJT 170A) is that the current flows out of the C terminal when the B-to-E input voltage is positive, and into the C terminal when the B-to-E input voltage is negative. The diamond transistor 170B is self-biased and, because the transconductance is constant over a wide range of collector currents, more linear than an ordinary transistor.

FIG. 5D illustrates an example of a circuit 162 that includes a diamond transistor 170B in accordance with some embodiments. The circuit 162 can be used as the amplifier circuit 160 in the configuration shown in FIG. 5A. In FIG. 5D, the diamond transistor 170B is used similarly to a CB amplifier. The E terminal of the diamond transistor 170B is coupled to the sense electrode 18A and to a current source 155, the B terminal is coupled to the bias voltage Vbias, and the C terminal is coupled to Vcc. Although not illustrated, the circuit 162 can include a resistance between the E terminal of the diamond transistor 170B and the nanopore 15.

A significant aspect of the circuit 162 is that the B terminal of the diamond transistor 170B is not grounded, but rather is connected to a bias voltage. With the circuit 162 as illustrated, the bias voltage biases the nanopore 15. (It is to be appreciated that the bias voltage Vbias can be any value, including zero.)

One benefit of the circuit 162 is that it is truly bipolar, which can be especially advantageous if the translocation of a molecule being sensed by the nanopore 15 is to be reversed. For example, if the nanopore 15 is included in a data storage device, and data is stored in molecules, those molecules can be read whether they pass through the nanopore 15 in the forward or reverse direction.

In some embodiments, the diamond transistor 170B is directly integrated onto the nanopore 15 substrate to mitigate the need for wiring and thereby reduce the input capacitance. In some embodiments, the diamond transistor 170B is provided as a separate component that is coupled to the nanopore 15 (e.g., via wiring).

Both of the circuit 161 and circuit 162 provide advantages as the amplifier circuit 160. Both the circuit 161 and circuit 162 allow the nanopore 15 to be read while reducing the effect of the parasitic capacitance 19 between the sense electrode 18A and counter electrode 18B. In essence, the circuit 161 and circuit 162 provide amplification while providing feedback on the sense electrode 18A to at least partially cancel the parasitic capacitance 19.

Those having ordinary skill in the art will appreciate that the circuit 161 and circuit 162 can include components that are not specifically illustrated (e.g., resistors, etc.). As will be appreciated, these components can be added to improve stability.

It will be appreciated that the bias voltage, Vbias, for the three-terminal device of the amplifier circuit 160 (e.g., the BJT 170A or the diamond transistor 170B) is separate from the voltage source 150 that biases the nanopore 15. One or both of Vbias and the voltage applied by the voltage source 150 may be adjustable.

It will also be appreciated that the nanopore 15 likely produces too little current (i.e., the amplitude of Is is too low) to cause the BJT 170A or diamond transistor 170B in the circuit 161 and circuit 162 to operate in a region in which they have high gain. Accordingly, it will be appreciated that the BJT 170A, diamond transistor 170B may be biased (e.g., by the current source 155 providing, e.g., 50-100 μA) so that they operate in a region in which they have sufficiently high gain.

Figure 6:
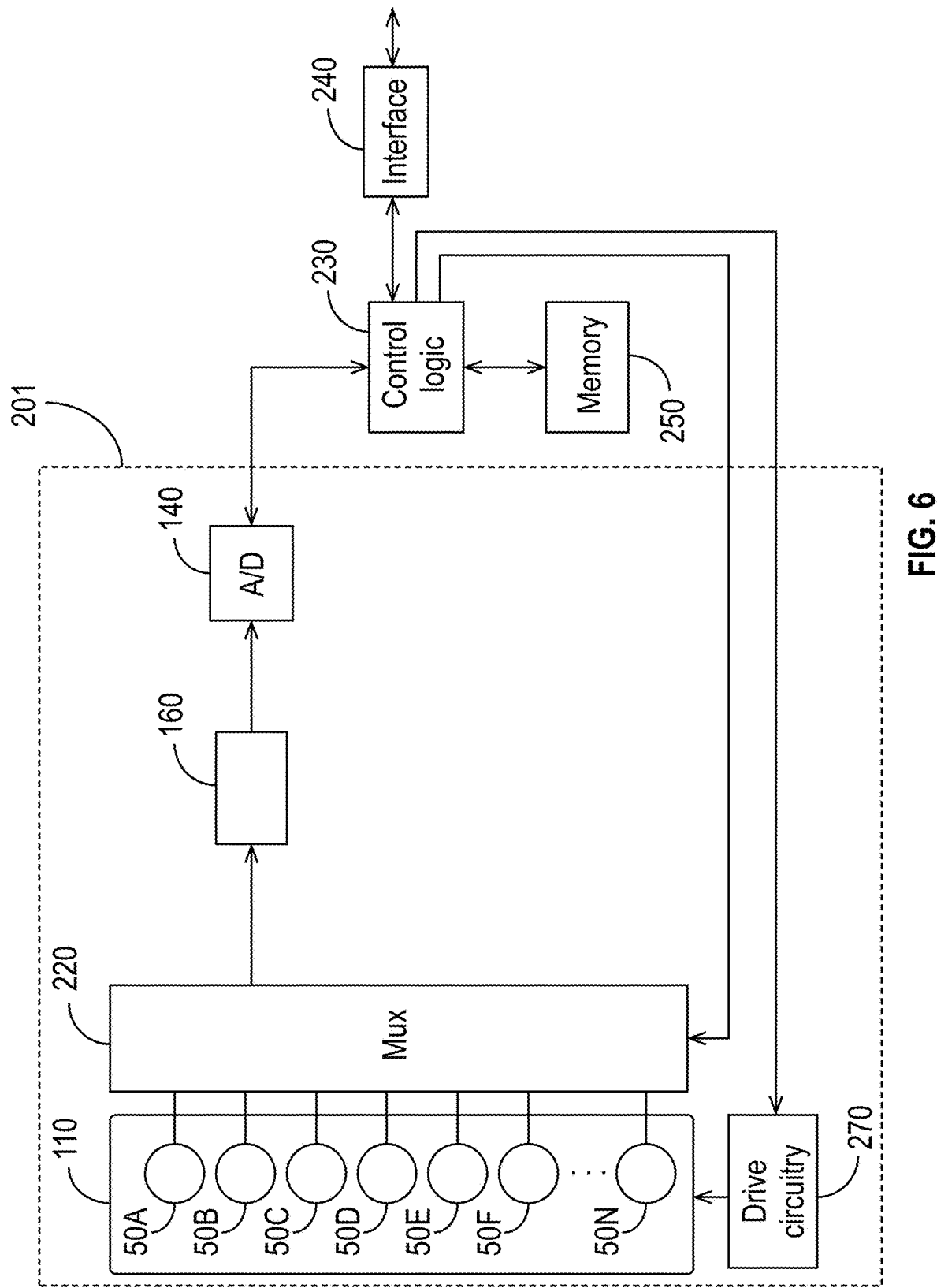
FIG. 6 illustrates an example of a system that includes an amplifier circuit shared by a plurality of nanopore units in accordance with some embodiments.

In the example system 200 shown in FIG. 5A, the amplifier circuit 160 is connected to a single nanopore units 50. In some embodiments, the amplifier circuit 160 is used to read multiple nanopores 15. FIG. 6 illustrates an example of a system 201 that includes an amplifier circuit 160 that can read multiple nanopore 15 in accordance with some embodiments. The amplifier circuit 160 may be, for example, the circuit 161 or the circuit 162 described above. In the illustrated example, the system 201 comprises an array 110 of nanopore units 50. In FIG. 6, the array 110 is shown as including at least the nanopore unit 50A, the nanopore unit 50B, the nanopore unit 50C, the nanopore unit 50D, the nanopore unit 50E, the nanopore unit 50F, and the nanopore unit 50N, but it is to be appreciated that the array 110 can include fewer or more nanopore units 50 than shown. Moreover, the use of the letter "N" in the last illustrated nanopore unit 50 is not intended to suggest that the array 110 of the system 201 includes any particular number of nanopore units 50. In general, the array 110 can include any number of nanopore units 50 (e.g., one or more).

In some embodiments, some or all of the nanopore units 50 of the array 110 share a counter electrode 18B but each nanopore 15 has its own sense electrode 18A with an individualize voltage. Such a configuration may be particularly advantageous from a manufacturing standpoint. For example, a continuous metal electrode on the back of a wafer could serve as a common counter electrode 18B for some or all of the nanopore units 50. This type of implementation would not require the back side of the wafer to be patterned, nor would it require a large number of wires to be brought from the back side of the wafer to the front side, which can be complicated.

The array 110 is coupled to a multiplexer 220. As shown in FIG. 6, the multiplexer 220 has a plurality of inputs, each corresponding to a respective one of the nanopore units 50 in the array 110, and a single output. The multiplexer 220 may be, for example, configured to cycle through individual nanopore units 50 of the array 110 to read the nanopores 15 in a systematic way (e.g., periodically, in accordance with a clock signal, in response to an instruction from the control logic 230 discussed below, etc.). Alternatively or in addition, the multiplexer 220 may be configured to select any one nanopore unit 50 in the array 110 at any time (e.g., when desirable or necessary) and to read its nanopore 15 (e.g., provide a signal representing its current to the amplifier circuit 160). Accordingly, as illustrated in FIG. 6, in the system 201, a plurality (some or all) of the nanopore units 50 in the array 110 are coupled to the multiplexer 220 and are selectable by the multiplexer 220.

As shown in the example of FIG. 6, the multiplexer 220 is coupled to and provides a signal corresponding to a selected nanopore unit 50 to the amplifier circuit 160. Referring back to FIG. 5A, the multiplexer 220 may provide the current Is corresponding to the selected nanopore 15 to the amplifier circuit 160. As explained above in the discussion of FIGS. 5A-5D, the amplifier circuit 160 comprises a three-terminal device. In the system 201 shown in FIG. 6, the first terminal of the three-terminal device is coupled to the multiplexer 220 output, the second terminal of the three-terminal device is coupled to a bias voltage source (to produce Vbias), and the third terminal of the three-terminal device is the output of the amplifier circuit 160.

As illustrated in FIG. 6, the amplifier circuit 160 of the system 201 provides an output signal (e.g., Vs of FIG. 5A) to the analog-to-digital converter 140 (or, generally, a digitizer). The analog-to-digital converter 140 is coupled to, and can provide signals to and receive signals from, control logic 230. As will be appreciated by those having ordinary skill in the art, the control logic 230 may be implemented in any suitable way (e.g., a processor, an application-specific integrated circuit (ASIC), field-programmable gate array (FPGA), etc.). In the example system 201, the control logic 230 is coupled to memory 250 and to an interface 240. The memory may be on-board (e.g., on an integrated circuit chip that includes some or all components of the system 201, etc.), or it may be external memory. The interface 240 may couple the system 201 to a processing device (e.g., the processing device 180 shown in FIG. 5A).

As shown in FIG. 6, the control logic 230 is coupled to memory 250, which may be on-chip or off-chip memory. Memory 250 may store information (e.g., computer-readable instructions) that can be used to read the nanopores 15 and/or to store read results.

The control logic 230 is also coupled to and configured to provide signals/instructions to the drive circuitry 270. The drive circuitry 270 is coupled to the array 110 and, as its name suggests, is the driver for at least one nanopore unit 50 of the array 110. For example, the drive circuitry 270 may include the voltage source 150 illustrated in FIG. 5A. The drive circuitry 270 is the power supply that biases the array 110, and it includes at least one drive circuit coupled to at least one nanopore unit 50.

The control logic 230 is also coupled to and configured to provide signals/instructions to the multiplexer 220. For example, the control logic 230 can provide a signal to cause the multiplexer 220 to cycle through the connected nanopore units 50 to allow the nanopore 15 currents to be read/measured. Alternatively or in addition, the control logic 230 can select a particular nanopore unit 50 connected to the multiplexer 220 by providing a signal to the multiplexer 220.

It is to be appreciated that the control logic 230, memory 250, and interface 240 are illustrated in FIG. 6 as external to the system 201, but this demarcation is solely for convenience of description. For example, FIG. 7, described below, includes multiple instantiations of the components of the system 201 shown in FIG. 6, as well as control logic and an interface. It is to be appreciated that the system 201 can include components or elements not illustrated in FIG. 6 as being part of the system 201. For example, the system 201 can include control logic 230, an interface 240, and/or memory 250.

Figure 7:
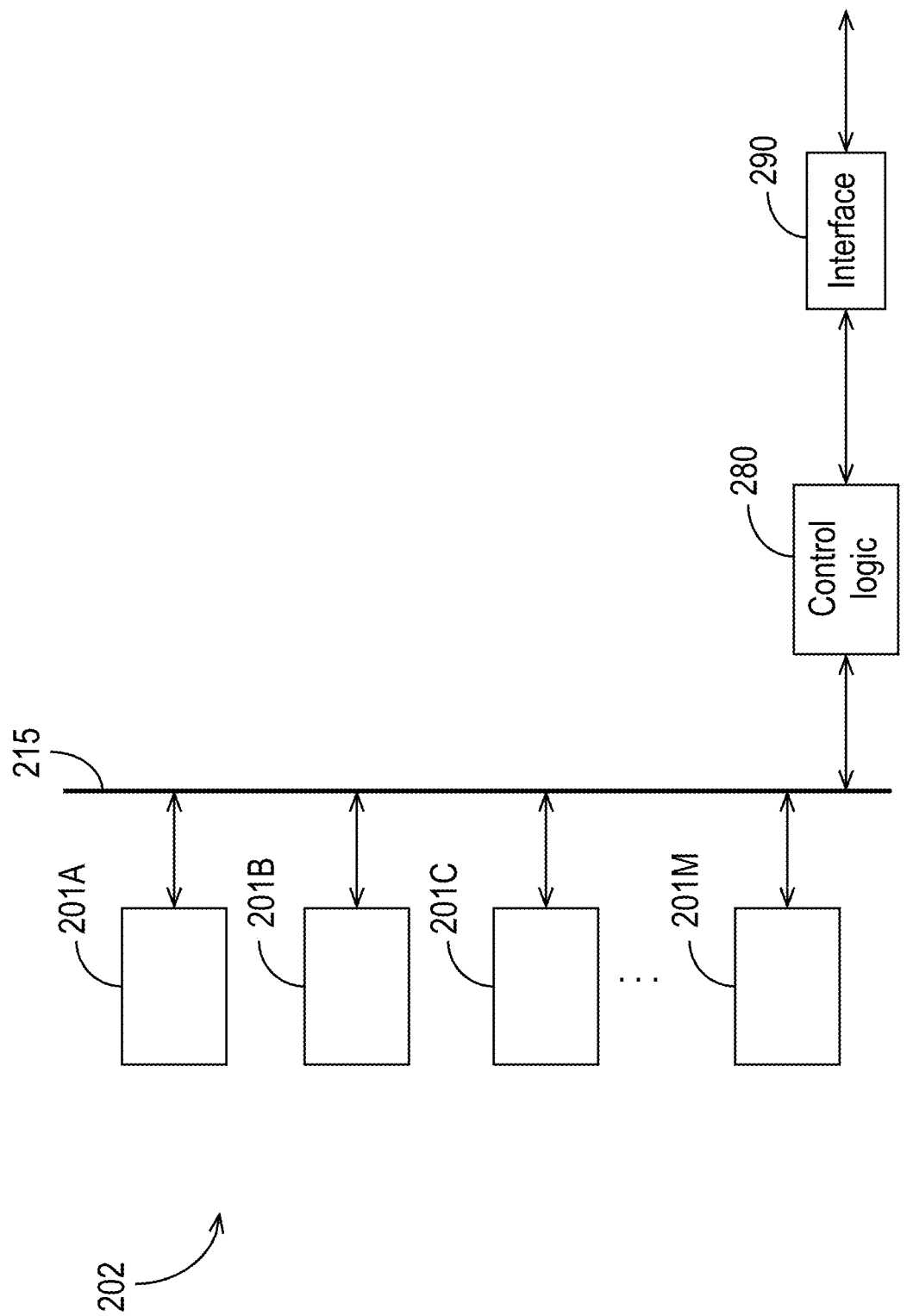
FIG. 7 illustrates another example of a system in accordance with some embodiments.

FIG. 7 illustrates another example of a system 202 in accordance with some embodiments. As illustrated, the system 202 includes one or more of the system 201 described above, thereby making the systems 201 subsystems of the system 202. In the example shown in FIG. 7, the system 202 includes a plurality of systems 201 as subsystems. FIG. 7 illustrates and labels the subsystem 201A, the subsystem 201B, the subsystem 201C, and the subsystem 201M, but it is to be appreciated that the system 202 can include any number of systems 201 as subsystems. Moreover, the use of the letter "M" in the last illustrated system 201 is not intended to suggest that the system 202 includes any particular number of instances of systems 201 as subsystems.

As described in the context of FIG. 6, multiple nanopore units 50 of each of the system 201 can share a counter electrode 18B. Furthermore, multiple systems 201 can share a counter electrode 18B. Thus, for example, some or all of the nanopore units 50 in subsystem 201A can share a counter electrode 18B with some or all of the nanopore units 50 in one or more of subsystem 201B, subsystem 201C, subsystem 201M, and/or any other subsystem in the system 202.

The subsystem 201A, subsystem 201B, subsystem 201C, . . . , subsystem 201M (collectively referred to as the "subsystems 201x") of FIG. 7 are coupled to a bus 215. The bus 215 may be any suitable wired or wireless communication channel that allows the subsystems 201x in the system 202 to communicate with the control logic 280. The control logic 280 is configured to provide instructions/commands to and receive information/data from the subsystems 201x. The control logic 280 may be configured to perform the functions of the control logic 230 shown in FIG. 6, but for all of the subsystems 201x of the system 202. The control logic 280 is also coupled to an interface 290, which is configured to provide information to and obtain information from the control logic 280. The interface 290 may be any suitable interface and may communicate, wirelessly and/or via a wired communication path, with downstream components (e.g., processor, memory) using any suitable protocol. For example, it may provide communication via Wi-Fi, Ethernet, USB, etc. The interface 290 may be configured to perform the functions of the interface 240 shown in FIG. 6. The system 202 may also include memory (not illustrated), which may serve the same purpose(s) as described above for the memory 250 of FIG. 6.

Figure 8:
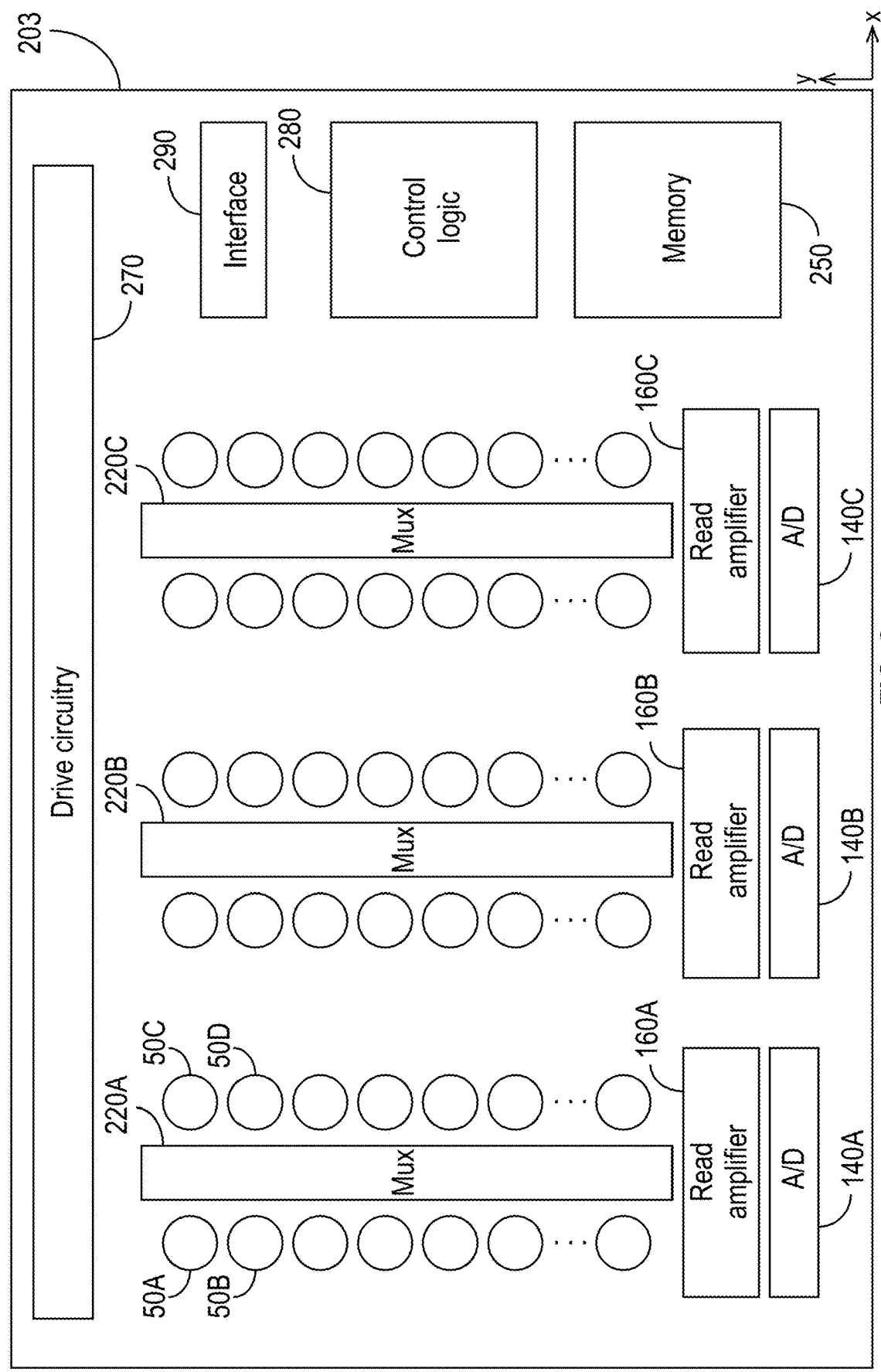
FIG. 8 illustrates another example of a system in accordance with some embodiments.

FIG. 8 illustrates an example of a system 203 in accordance with some embodiments. The system 203 may be an implementation of the system 202 shown in FIG. 7. The system 203 may be, for example, implemented as an integrated circuit chip that allows molecules to be detected. FIG. 8 is a diagram showing a plan view (e.g., in an x-y plane perpendicular to the x-z plane shown in FIG. 1 and others herein) of the system 203. As shown, the system 203 includes a plurality of nanopore units 50. To avoid obscuring the drawing, only four nanopore units 50 are labeled: nanopore unit 50A, nanopore unit 50B, nanopore unit 50C, and nanopore unit 50D.

As explained in the discussion of FIG. 6, the nanopore units 50 are coupled to multiplexers 220. In FIG. 8, respective pluralities (subsets) of the nanopore units 50 are coupled to the multiplexer 220A, multiplexer 220B, and multiplexer 220C. Coupled to each of the multiplexers 220 (e.g., as illustrated in FIG. 6) is a respective a respective amplifier circuit 160 and a respective analog-to-digital converter 140. Specifically, multiplexer 220A is coupled to amplifier circuit 160A and analog-to-digital converter 140A; multiplexer 220B is coupled to amplifier circuit 160B and analog-to-digital converter 140B; and multiplexer 220C is coupled to amplifier circuit 160C and analog-to-digital converter 140C. The system 203 also includes drive circuitry 270, an interface 290, control logic 280, and memory 250. These components were described above in the discussion of FIGS. 7 and/or 8. That discussion applies here and is not repeated.

As described above in the context of FIG. 6 and FIG. 7, some or all of the nanopore units 50 can share a counter electrode 18B. In the plan view of FIG. 8, a common counter electrode 18B may be situated, for example, on the bottom of a wafer so that the back side of the wafer does not need to be patterned.

In the foregoing description and in the accompanying drawings, specific terminology has been set forth to provide a thorough understanding of the disclosed embodiments. In some instances, the terminology or drawings may imply specific details that are not required to practice the invention.

The term "diamond transistor" is used herein to describe a device that approximates ideal transistor behavior, at least under some conditions. As explained above, other names for the diamond transistor include operational transconductance amplifier, voltage-controlled current source, transconductor, macro transistor, and second-generation current conveyor (CCII+). The use of a diamond transistor in the examples is not meant to be limiting. Other structures that perform similarly or identically to a diamond transistor are also suitable, regardless of what they are called.

To avoid obscuring the present disclosure unnecessarily, well-known components are shown in block diagram form and/or are not discussed in detail or, in some cases, at all.

Unless otherwise specifically defined herein, all terms are to be given their broadest possible interpretation, including meanings implied from the specification and drawings and meanings understood by those skilled in the art and/or as defined in dictionaries, treatises, etc. As set forth explicitly herein, some terms may not comport with their ordinary or customary meanings.

As used in the specification and the appended claims, the singular forms "a," "an" and "the" do not exclude plural referents unless otherwise specified. The word "or" is to be interpreted as inclusive unless otherwise specified. Thus, the phrase "A or B" is to be interpreted as meaning all of the following: "both A and B," "A but not B," and "B but not A." Any use of "and/or" herein does not mean that the word "or" alone connotes exclusivity.

As used in the specification and the appended claims, phrases of the form "at least one of A, B, and C," "at least one of A, B, or C," "one or more of A, B, or C," and "one or more of A, B, and C" are interchangeable, and each encompasses all of the following meanings: "A only," "B only," "C only," "A and B but not C," "A and C but not B," "B and C but not A," and "all of A, B, and C."

To the extent that the terms "include(s)," "having," "has," "with," and variants thereof are used in the detailed description or the claims, such terms are intended to be inclusive in a manner similar to the term "comprising," i.e., meaning "including but not limited to."

The terms "exemplary" and "embodiment" are used to express examples, not preferences or requirements.

The term "coupled" is used herein to express a direct connection/attachment as well as a connection/attachment through one or more intervening elements or structures.

The terms "over," "under," "between," and "on" are used herein refer to a relative position of one feature with respect to other features. For example, one feature disposed "over" or "under" another feature may be directly in contact with the other feature or may have intervening material. Moreover, one feature disposed "between" two features may be directly in contact with the two features or may have one or more intervening features or materials. In contrast, a first feature "on" a second feature is in contact with that second feature.

The term "substantially" is used to describe a structure, configuration, dimension, etc. that is largely or nearly as stated, but, due to manufacturing tolerances and the like, may in practice result in a situation in which the structure, configuration, dimension, etc. is not always or necessarily precisely as stated. For example, describing two lengths as "substantially equal" means that the two lengths are the same for all practical purposes, but they may not (and need not) be precisely equal at sufficiently small scales. As an example, a structure that is "substantially vertical" would be considered to be vertical for all practical purposes, even if it is not precisely at 90 degrees relative to horizontal.

The drawings are not necessarily to scale, and the dimensions, shapes, and sizes of the features may differ substantially from how they are depicted in the drawings.

Although specific embodiments have been disclosed, it will be evident that various modifications and changes may be made thereto without departing from the broader spirit and scope of the disclosure. For example, features or aspects of any of the embodiments may be applied, at least where practicable, in combination with any other of the embodiments or in place of counterpart features or aspects thereof. Accordingly, the specification and drawings are to be regarded in an illustrative rather than a restrictive sense.

The invention claimed is:

1. A system for detecting molecules, the system comprising:
   a nanopore array comprising a plurality of nanopore units, each of the plurality of nanopore units comprising a respective nanopore, a respective sense electrode, and a respective counter electrode, each respective sense electrode for detecting a current associated with the respective nanopore;
   a multiplexer coupled to the nanopore array;
   an amplifier circuit coupled to an output of the multiplexer, the amplifier circuit comprising a three-terminal device, wherein a first terminal of the three-terminal device is low impedance and coupled to the output of the multiplexer, a second terminal of the three-terminal device is high impedance and coupled to a bias voltage source, and a third terminal of the three-terminal device is a high-impedance output of the amplifier circuit; and
   control logic coupled to the multiplexer and configured to control the multiplexer to select a particular nanopore unit of the plurality of nanopore units and to couple the respective sense electrode of the particular nanopore unit to the amplifier circuit, wherein the particular nanopore unit is any one of the plurality of nanopore units,
   wherein:
   an impedance of the first terminal is less than an impedance of the second terminal, the impedance of the first terminal is less than an impedance of the third terminal, the respective sense electrode is configured to:
      in cooperation with the respective counter electrode, detect a current associated with the respective nanopore, and
      provide the detected current to the first terminal of the three-terminal device, and
   the third terminal of the three-terminal device is configured to provide a signal representing the detected current to a downstream component.

2. The system recited in claim 1, wherein the downstream component is a digitizer, and wherein the digitizer coupled is coupled to the third terminal of the three-terminal device and is configured to generate a digitized signal from the signal representing the detected current.

3. The system recited in claim 2, further comprising a processor coupled to an output of the digitizer.

4. The system recited in claim 1, wherein three-terminal device comprises a bi-polar junction transistor (BJT), and wherein the first terminal is an emitter of the BJT, the second terminal is a base of the BJT, and the third terminal is a collector of the BJT.

5. The system recited in claim 4, wherein the BJT is integrated onto a substrate of the nanopore array.

6. The system recited in claim 1, wherein three-terminal device comprises a diamond transistor, and wherein the first terminal is an E terminal of the diamond transistor, the second terminal is a B terminal of the diamond transistor, and the third terminal is a C terminal of the diamond transistor.

7. The system recited in claim 6, wherein the diamond transistor is integrated onto a substrate of the nanopore array.

8. The system recited in claim 1, wherein the three-terminal device comprises at least one of: a bi-polar junction transistor (BJT), a diamond transistor, a CMOS transistor, an operational transconductance amplifier, a voltage-controlled current source, a transconductor, a macro transistor, or a second-generation current conveyor (CCII+).

9. The system recited in claim 1, wherein the three-terminal device is integrated onto a substrate of the nanopore array.

10. The system recited in claim 1, wherein a first nanopore unit of the nanopore array includes a first nanopore, a first sense electrode, and a first counter electrode, and a second nanopore unit of the nanopore array includes a second nanopore, a second sense electrode, and a second counter electrode, wherein:
the multiplexer is situated between and coupled to the first nanopore unit and the first terminal of the three-terminal device;
the second sense electrode is coupled to the multiplexer; and
the control logic is configured to select one of the first sense electrode or the second sense electrode.

11. The system recited in claim 10, further comprising:
drive circuitry coupled to the first nanopore unit and to the second nanopore unit and configured to create a first potential between the first sense electrode and the first counter electrode and/or create a second potential between the second sense electrode and the second counter electrode.

12. The system recited in claim 11, wherein the downstream component is a digitizer, and wherein the digitizer coupled is coupled to the third terminal of the three-terminal device and is configured to generate a digitized signal from the signal representing the detected current.

13. The system recited in claim 12, further comprising a processor coupled to an output of the digitizer.

14. The system recited in claim 10, wherein the first counter electrode and the second counter electrode are coupled to a common bias voltage source.

15. The system recited in claim 10, wherein the first counter electrode and the second counter electrode are a same electrode.

16. A system for detecting molecules, the system comprising:
a nanopore array comprising a plurality of nanopore units, each of the plurality of nanopore units comprising a respective nanopore, a respective sense electrode, and a respective counter electrode, each respective sense electrode for detecting a current associated with the respective nanopore;
a multiplexer coupled to the nanopore array;
an amplifier circuit coupled to an output of the multiplexer, the amplifier circuit comprising a three-terminal device, wherein a first terminal of the three-terminal device is coupled to the output of the multiplexer, a second terminal of the three-terminal device is coupled to a bias voltage source, and a third terminal of the three-terminal device is an output of the amplifier circuit, wherein the first terminal of the three-terminal device is a low-impedance terminal, and the second terminal of the three-terminal device is a high-impedance terminal; and
control logic coupled to the multiplexer and configured to control the multiplexer to select a particular nanopore unit of the plurality of nanopore units and to couple the respective sense electrode of the particular nanopore unit to the amplifier circuit, wherein the particular nanopore unit is any one of the plurality of nanopore units.

17. The system recited in claim 16, further comprising drive circuitry coupled to the nanopore array.

18. The system recited in claim 16, wherein the three-terminal device comprises a bi-polar junction transistor (BJT), and wherein the first terminal is an emitter of the BJT, the second terminal is a base of the BJT, and the third terminal is a collector of the BJT.

19. The system recited in claim 16, wherein the three-terminal device comprises a diamond transistor, and wherein the first terminal is an E terminal of the diamond transistor, the second terminal is a B terminal of the diamond transistor, and the third terminal is a C terminal of the diamond transistor.

20. The system recited in claim 16, wherein the three-terminal device comprises at least one of: a bi-polar junction transistor (BJT), a diamond transistor, a CMOS transistor, an operational transconductance amplifier, a voltage-controlled current source, a transconductor, a macro transistor, or a second-generation current conveyor (CCII+).

21. The system recited in claim 16, wherein the three-terminal device is integrated onto a substrate of the nanopore array.

22. The system recited in claim 16, wherein the third terminal of the three-terminal device is a current source terminal.

23. The system recited in claim 16, wherein the control logic is further configured to:
control the multiplexer to select a second nanopore unit of the plurality of nanopore units for reading.

24. The system recited in claim 16, wherein each respective counter electrode is coupled to a common voltage source.

25. The system recited in claim 16, wherein each respective counter electrode is a same counter electrode.

26. The system recited in claim 16, further comprising:
a digitizer coupled to the output of the amplifier circuit, wherein the digitizer is configured to generate a digitized signal from the current associated with the respective nanopore.

27. The system recited in claim 26, further comprising a processor coupled to an output of the digitizer.

28. The system recited in claim 16, wherein the nanopore array is a first nanopore array, the plurality of nanopore units is a first plurality of nanopore units, the multiplexer is a first multiplexer, the amplifier circuit is a first amplifier circuit, and the three-terminal device is a first three-terminal device, and further comprising:
a second nanopore array comprising a second plurality of nanopore units, each of the second plurality of nanopore units comprising a respective nanopore, a respective sense electrode, and a respective counter electrode, each respective sense electrode for detecting a current associated with the respective nanopore;
a second multiplexer coupled to the second nanopore array; and
a second amplifier circuit coupled to an output of the second multiplexer, the second amplifier circuit comprising a second three-terminal device, wherein a first terminal of the second three-terminal device is coupled to the output of the second multiplexer, a second terminal of the second three-terminal device is coupled to the bias voltage source, and a third terminal of the second three-terminal device is an output of the second amplifier circuit, and wherein the control logic is further coupled to the second multiplexer and is configured to control the second multiplexer to select a particular nanopore unit of the second plurality of nanopore units and to couple the respective sense electrode of the particular nanopore unit of the second plurality of nanopore units to the second amplifier circuit, wherein the particular nanopore unit of the second plurality of nanopore units is any one of the second plurality of nanopore units.

29. The system recited in claim 28, wherein:
the first three-terminal device comprises a first bi-polar junction transistor (BJT), wherein the first terminal of the first three-terminal device is an emitter of the first BJT, the second terminal of the first three-terminal device is a base of the first BJT, and the third terminal of the first three-terminal device is a collector of the first BJT, and
the second three-terminal device comprises a second BJT, wherein the first terminal of the second three-terminal device is an emitter of the second BJT, the second terminal of the second three-terminal device is a base of the second BJT, and the third terminal of the second three-terminal device is a collector of the second BJT.

30. The system recited in claim 28, wherein:
the first three-terminal device comprises a first diamond transistor, wherein the first terminal of the first three-terminal device is an E terminal of the first diamond transistor, the second terminal of the first three-terminal device is a B terminal of the first diamond transistor, and the third terminal of the first three-terminal device is a C terminal of the first diamond transistor, and
the second three-terminal device comprises a second diamond transistor, wherein the first terminal of the second three-terminal device is an E terminal of the second diamond transistor, the second terminal of the second three-terminal device is a B terminal of the second diamond transistor, and the third terminal of the second three-terminal device is a C terminal of the first diamond transistor.

31. The system recited in claim 28, wherein the first three-terminal device and/or the second three-terminal device comprises at least one of: a bi-polar junction transistor (BJT), a diamond transistor, a CMOS transistor, an operational transconductance amplifier, a voltage-controlled current source, a transconductor, a macro transistor, or a second-generation current conveyor (CCII+).

32. The system recited in claim 28, wherein:
each respective counter electrode of the first nanopore array is coupled to a first common voltage source, and
each respective counter electrode of the second nanopore array is coupled to a second common voltage source.

33. The system recited in claim 32, wherein the first common voltage source and the second common voltage source are a same voltage source.

34. The system recited in claim 28, wherein:
each respective counter electrode of the first nanopore array is a first common counter electrode; and
each respective counter electrode of the second nanopore array is a second common counter electrode.

35. The system recited in claim 28, wherein each respective counter electrode of the first nanopore array and each respective counter electrode of the second nanopore array is a common counter electrode.

36. The system recited in claim 28, further comprising:
a first digitizer coupled to the output of the first amplifier circuit;
a second digitizer coupled to the output of the second amplifier circuit; and
a processor coupled to a first output of the first digitizer and to a second output of the second digitizer.

* * * * *